(12) United States Patent
Neuberger (10) Patent No.: US 6,385,221 B1
(45) Date of Patent: May 7, 2002

(54) MULTIPLEXED MEDICAL DIODE LASER SYSTEM

(75) Inventor: Wolfgang Neuberger, F. T. Labuan (MY)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 09/344,816

(22) Filed: Jun. 25, 1999

(51) Int. Cl.⁷ .................................................. H01S 3/00
(52) U.S. Cl. .................. 372/38.02; 372/29.05
(58) Field of Search ............................ 372/38.02, 29.05

(56) References Cited

U.S. PATENT DOCUMENTS 5,936,986 A * 8/1999 Cantatore et al. ........ 372/38.02
6,044,095 A * 3/2000 Asano et al. .................. 372/38

* cited by examiner

Primary Examiner—Leon Scott, Jr.
(74) Attorney, Agent, or Firm—Bolesh J. Skutnik; B. J. Associates

(57) ABSTRACT

A multiplexed medical diode laser system is described that increases power available for applications that require approximately 760 nm or shorter wavelength radiation. Radiation from a diode laser emitter or emitter group is multiplexed with radiation from other diode laser emitters or emitter groups into a single fiber. The diode laser emitters or emitter groups are injected intermittently with current by transistors and thus, a quasi-cw diode laser source particularly useful for PDT is available. Since the radiation is multiplexed, diode laser emitters or emitter groups can be operated at optimal duty factors and generate less thermal energy, thereby increasing efficiency and power output of the system while maintaining at least near cw output. In a preferred embodiment, large peak and average output powers are obtained with a combination of fast switching transistors that regulate the duty factor of diode laser emitters or emitter groups, and suitable optics that multiplex the outputs.

19 Claims, 6 Drawing Sheets

MULTIPLEXED MEDICAL DIODE LASER SYSTEM

BACKGROUND OF THE INVENTION

1. Field of the Invention

The present invention relates to diode laser devices that employ laser sources with significant activation thresholds and high temperature sensitivities, which are capable of delivering quasi-continuous or near-continuous wave radiation energy.

2. Information Disclosure Statement

Diode light energy sources that have significant activation thresholds and high temperature sensitivities are rarely employed for applications that require laser energy having wavelengths in the visible red to near IR region because the output power at these wavelengths is limited to an ineffective level. Notably, these sources are seldom employed for applications in photodynamic therapy (PDT), which typically require light energy in the 600–760 nm range, or for environmental sensing and monitoring applications, which require light energy in the 3–3.5 $\mu$m range.

PDT is gaining importance both for cancer and non-cancer applications. Typically, this therapy begins with the application of a photosensitizer that may be topically applied, injected, or intravenously introduced to a treatment site. After a suitable time interval depending on certain properties of the photosensitizer, radiation energy in a suitable wavelength band is selectively applied for a predetermined duration and intensity to the target site.

The basic concept of PDT is that certain molecules function as photosensitizers that absorb light of certain wavelengths. If light energy of the proper wavelength is delivered to the photosensitizer, it stores the energy from the photons by increasing its energy to a higher level called a triplet state. Inside the body, some of the excited photosensitizer molecules transfer the stored energy to nearby oxygen molecules, exciting them to a higher energy level called a singlet state. Singlet oxygen is a highly reactive gas that rapidly oxidizes essential cellular components that surround it, and in a living cell this oxidation causes necrosis.

The choice of wavelength depends on the optical absorption characteristics of the photosensitizer, but red light has been favored for its absorption by the photosensitizer, and ability to reach a large tissue volume. A clinically useful photosensitizer should be non-toxic at useful doses, and should concentrate in diseased tissue by either selective uptake or retention. Also, the photosensitizer should be photochemically efficient and ideally be activated by tissue penetrating light (>600 nm). Most commonly, photosensitizers used in PDT consist of a hematoporphyrin derivative (HpD) such as porfimer sodium, or Photofrin. Although the mechanism of HpD's preferential location in malignant cells is uncertain, the total time that the derivatives are retained in the malignant tissue is much longer than in nonmalignant tissue, where it generally clears within 24–72 hours. As a result, there is a "window" of time in which the physician can exploit the differences in HpD concentrations to cause selective photodegradation of malignant tissue.

After photosensitizer administration, a delay of 24–72 hours allows for HpD to be expelled from healthy tissue, and the malignant tissue is irradiated with visible red light tuned to approximately 630 nm. Shortly after administering treatment, the tumor becomes necrotic and, when effectively treated, the tumor becomes a nonpalpable scab that is usually sloughed off within a few days. A high therapeutic ratio and relative lack of morbidity have made PDT a very attractive form of therapy.

While some forms of disease, such as skin disease, are accessible by a wider variety of light delivery systems, others occur inside the body and light energy must be brought to the treatment site using an optical fiber with a suitably configured tip. PDT is most commonly used to alleviate symptoms and diseases associated with cancers of the brain, head, neck, esophagus, skin, colon, and bladder, although PDT treatment can also be applied to other diseases. An example of the latter is age related macular degeneration, one of the most common causes of blindness in patients over 50 years of age. The "wet" form of this disease, responsible for 90% of the severe vision loss associated with this condition, is due to choroidal neovascularization, the proliferation of abnormal blood vessels from the choroid, between the retina and the sclera. Fluid leaking from these blood vessels and development of scar tissue are the main reasons for loss of central vision. PDT can be used to slow down the debilitating effects of the disease. The current treatment is relatively unselective, and the heat used to destroy abnormal vessels can induce severe damage to the overlying retina. Application of PDT for this disease involves an intravenous injection of a photosensitizer such as benzoporphyrin derivative monoacid ring A, followed by photoactivation with non-thermal radiation at a wavelength specific for the dye.

PDT is advantageous compared to conventional treatments such as surgery because the procedure can often be carried out in a clinical setting, i.e. in treatment rooms rather than operating rooms. Also, PDT is minimally invasive, safe, cost effective, and highly selective.

High laser powers may not be advantageous in PDT because high power densities can cause tissue ablation, and a main mechanism of PDT is to activate the photosensitizer. However, the laser power must be sufficient (3–4 watts) to effectively penetrate tissue and allow treatment distribution over a large area (several cm). Thus, to maximize necrosis, it is advantageous to employ a laser system for PDT that emits radiation having an activating wavelength of a chosen photosensitizer, and is powerful enough to penetrate to a desired depth without damaging the surrounding areas.

Certain applications, such as the prevention of cell proliferation, that cause restenosis following balloon angioplasty, require delivery of high energy levels through very thin optical fibers (preferably 200 $\mu$m diameter). Output powers of 10 to 15 W would be advantageously used, without the risk of thermal damage, because the output radiation is emitted from a long length (several cm) cylindrical tip, that can also be cooled. Short irradiation times are of advantage, as this limits the duration of the treatment.

Continuous wave (cw) sources are preferred in PDT because they can be evenly applied at a treatment site to yield reproducible results and limited treatment times. Moreover, a cw source maintains the greatest amount of photosensitizer in an excited state that leads to elevated levels of oxygen singlets within the diseased tissue.

Due to the inefficiency of semiconductor materials, relatively few diode laser sources are presently available for PDT. The heat generated by a diode laser source often limits the power available at a treatment site to an ineffective level. Diode lasers, however, are very effective at longer operating wavelengths such as 808 nm, and 980 nm, because material science has increased the efficiency of the diodes at these wavelengths. This efficiency is lacking at lower wavelengths, i.e. below about 760 nm, and currently, no diode laser source operating at wavelengths used in PDT is able to effectively emit important photosensitizer activating wavelengths, such as 630 nm, 652 nm, or 732 nm, with sufficient average output power of approximately 3 to 4 watts. In fact, for use in PDT, the Food and Drug Administration (FDA) has only approved a KTP frequency doubled Nd:YAG pumped dye laser and an argon-ion pumped dye laser. These systems are inherently difficult to use. They are bulky, can contain toxic dyes, consume large amounts of electricity, need regular maintenance, and cost well over $100,000.

Diode lasers have distinct advantages over these classical lasers and other solid state lasers including compact size, lower power consumption, and lower maintenance costs. They are much more user friendly, and since a diode laser system typically costs much less than state of the art solid state lasers, laser applications are more available to the public. To take full advantage of the diode laser, there is a need for a diode based laser system capable of transmission of wavelengths within the visible red to near IR region and within the 3.0–3.5 $\mu$m range. Thus, the current deficiencies of material science may be overcome and diode lasers could replace solid state lasers in the many applications which require these wavelengths of light energy.

OBJECTS AND SUMMARY OF THE INVENTION

It is therefore an object of the present invention to address the need for a diode laser system that may effectively be employed for use in applications that require light energy having a wavelength in the visible red to near IR range or the 3.0–3.5 $\mu$m range.

Another object of the present invention is to provide a diode laser system that multiplexes outputs from diode laser emitters or emitter groups that are injected with drive currents by transistors.

Still another object of the present invention is to provide a diode laser system that can emit radiation having a wavelength below 760 nm with sufficient power necessary for activation of common photosensitizers used in PDT.

It is an aim of the present invention to provide a pulsed laser device utilizing a diode laser source that simulates quasi-continuous wave output to allow for maximum activation of a chosen photosensitizer, leading to necrosis of diseased tissue.

It is a further aim of the present invention to provide a diode laser system that has a narrow and flexible delivery component with a small cross sectional diameter. Maneuverability of the delivery component is thus increased, and it is more easily guided to a treatment site within the mammalian body.

Briefly stated, the present invention provides a multiplexed medical diode laser system that increases power available for applications that require light energy having a wavelength in the visible red to near IR range or 3.0–3.5 $\mu$m range. Radiation from a diode laser emitter or emitter group is multiplexed with radiation from other diode laser emitters or emitter groups into a single optics. The diode laser emitters or emitter groups are injected intermittently with current by transistors and thus, a quasi-cw diode laser source may be available. Since the radiation is multiplexed, diode laser emitters or emitter groups can be operated at optimal duty factors and generate less thermal energy, thereby increasing efficiency while maintaining at least near cw output. In a preferred embodiment, large peak and average output powers are obtained with a combination of fast switching transistors that regulate the duty factor of diode laser emitters or emitter groups, and suitable optics that multiplex the outputs.

The above, and other objects, features and advantages of the present invention will become apparent from the following detailed description read in conjunction with the accompanying drawings.

DETAILED DESCRIPTION OF PREFERRED EMBODIMENTS

Diode light energy sources that have significant activation thresholds and high temperature sensitivities are rarely employed for applications that require laser energy having wavelengths in the visible red to near IR region or the 3.0–3.5 $\mu$m range because the output power at these wavelengths is limited to an ineffective level. Notably, these sources are seldom employed for applications in photodynamic therapy (PDT), which typically require light energy in the 600–760 nm range, or for environmental sensing and monitoring applications, which typically require 3.0 $\mu$m light energy. The present invention provides a light energy delivery device that employs energy sources with these characteristics, and is capable of delivering effective power for applications in these regions, which previously was hardly attainable. Output power necessary for these applications is accomplished by injecting current into diode laser emitters or emitter groups at a high repetition rate, i.e. >1 kHz, and multiplexing their output. The term "multiplex" is used to describe a system where radiation from at least two diode laser emitters is transported through a single transmitting element to the treatment site.

Figure 1:
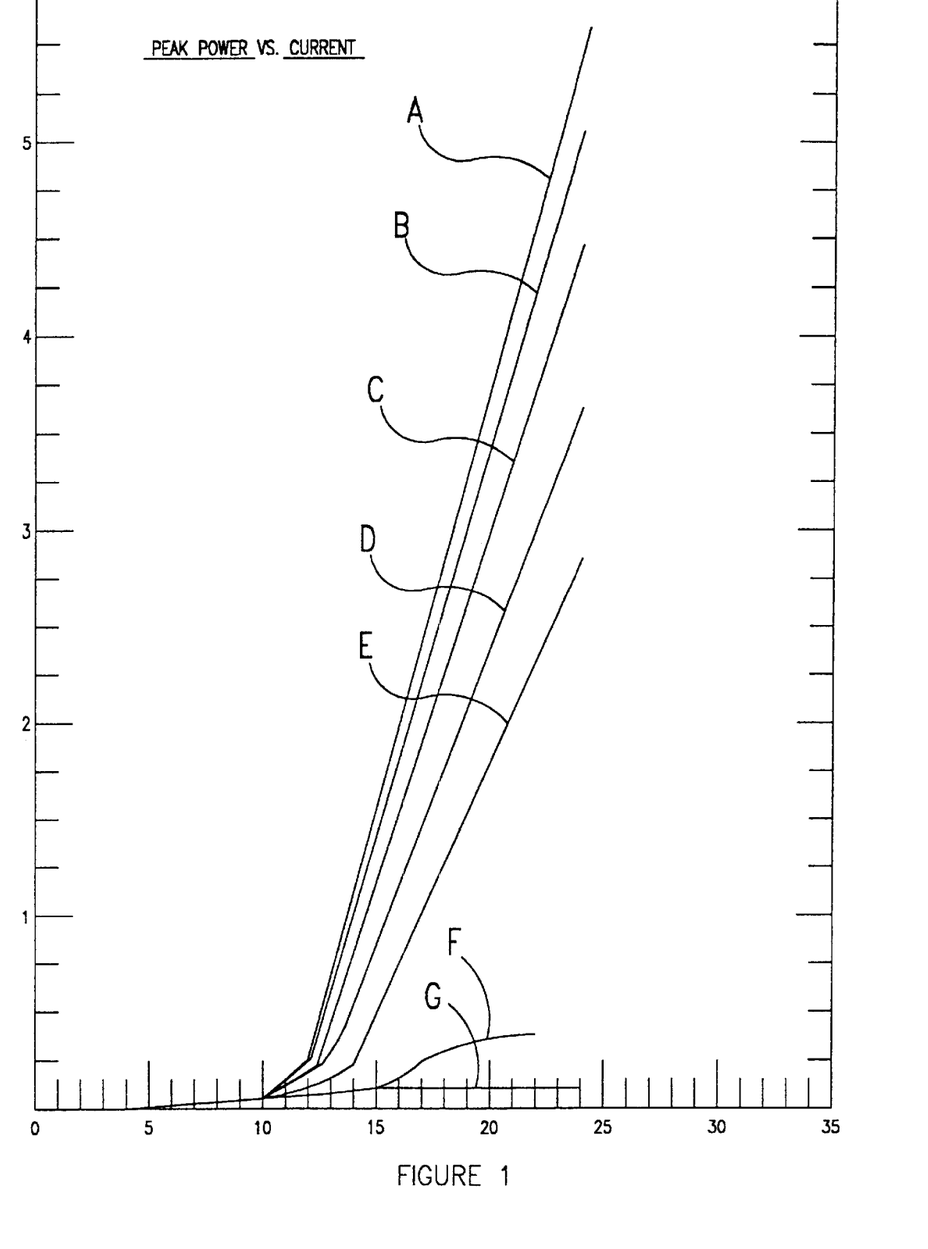
FIG. 1 illustrates the peak output power of a diode laser emitter group operating at 651 nm.
Figure 2:
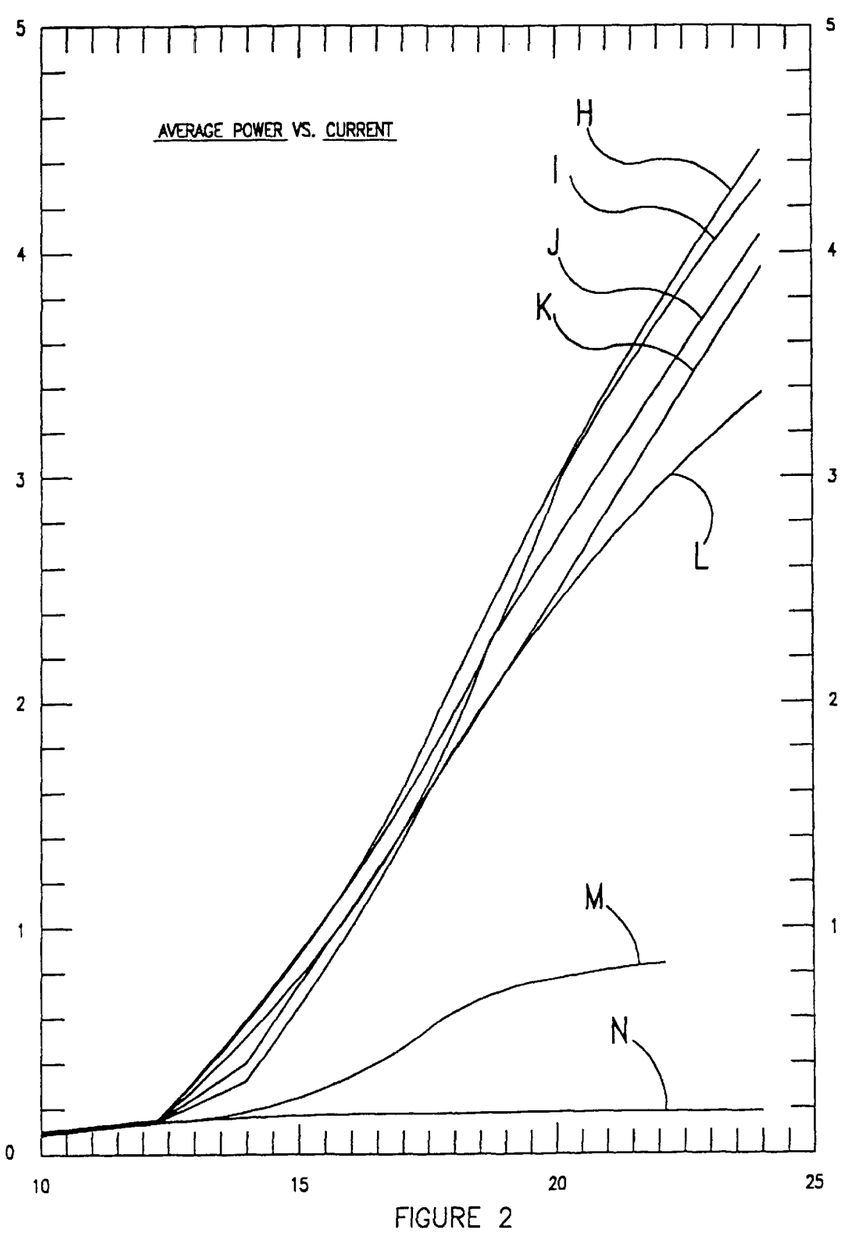
FIG. 2 illustrates the average output power of the diode laser emitter group operating in FIG. 1.

FIG. 1 and FIG. 2 both illustrate the output power achievable by varying the duty factor of a ten diode laser emitter bar with 150 $\mu$m stripes spaced on 1000 $\mu$m centerlines emitting at 651 nm. All diode laser emitters are driven simultaneously and their outputs are multiplexed. FIG. 1 surprisingly shows that at a duty factor of 30% (active 30% of the time and dormant 70% of the time) the system, operating at 1 kHz, yields the greatest peak output power, approximately 11.21 watts at 24 amps. As the duty factor of the system is increased, peak output power decreases. At the same peak current of 24 amps, the system yields a peak output power of 10.18 watts when operating at a 40% duty factor, 8.82 watts at 50%, 7.25 watts at 60%, and 5.70 watts at 70%.

The same diode laser emitter group under identical conditions emitted far less peak output power when operated continuously compared to non-cw operation. At 24 amps of input current, the system operating continuously with an aluminum nitride thermoplastic pad yielded only 0.82 watts of peak output power, and merely 0.16 watts with an indium foil pad. Notably, at a 30% duty factor and 24 amps, the system yields above an order of magnitude, almost 1400% greater output power than when operating continuously.

Several factors may contribute to the increase in peak output power when operating the system non-continuously. Diodes lasers emitting in these wavelength ranges (i.e. 600–760 nm and 3.0–3.5 $\mu$m) have unusually high temperature sensitivities which previously have limited their use for the important applications such as PDT (which typically require light energy having a wavelength in the 600–760 nm range), because the diode laser emitters inefficiently convert input energy to output power. By decreasing the duty factor of the diode laser emitters or emitter groups, less average thermal energy is produced at the diode, and negative effects due to temperature increases on a diode laser emitter are minimized. The radiation from diode laser emitters operating at an optimal duty factor can be multiplexed with radiation from other diode laser emitters or emitter groups that are injected intermittently with current, and a quasi-cw diode laser source employable for PDT is thus available.

Another negative effect of temperature on the system relates to the physical properties of the semiconductor materials. As the temperature of a diode laser emitter is increased, the energy bandgap decreases. The energy bandgap is the difference in energy of the conduction band (free electrons within the n and p layers) and the valence band (bound electrons in crystal) and is roughly equal to the voltage that must be applied to a semiconductor diode before current begins to flow. The shrinkage of the bandgap leads to electron leakage from the active layer to the p-type cladding which can further decrease output power because less electrons "fall" into holes and emit photons of energy.

The shrinkage of the bandgap also causes an increase in output wavelength because the bandgap is roughly related to wavelength by:

$$\lambda = 1240/E_g \qquad (1)$$

For example, GaAs has a bandgap (Eg) of 1.4 eV, so it produces photons of wavelengths approximately 850 nm. Thus, as the bandgap decreases, emission wavelength increases. Typically, the overall increase in wavelength with temperature is approximately 0.05 nm/° C. (Ettenberg, Michael, "Fundamentals of Semiconductor Lasers," Photonics Spectra. Vol. 32, pgs. 148–53 (1998)).

Figure 3A:
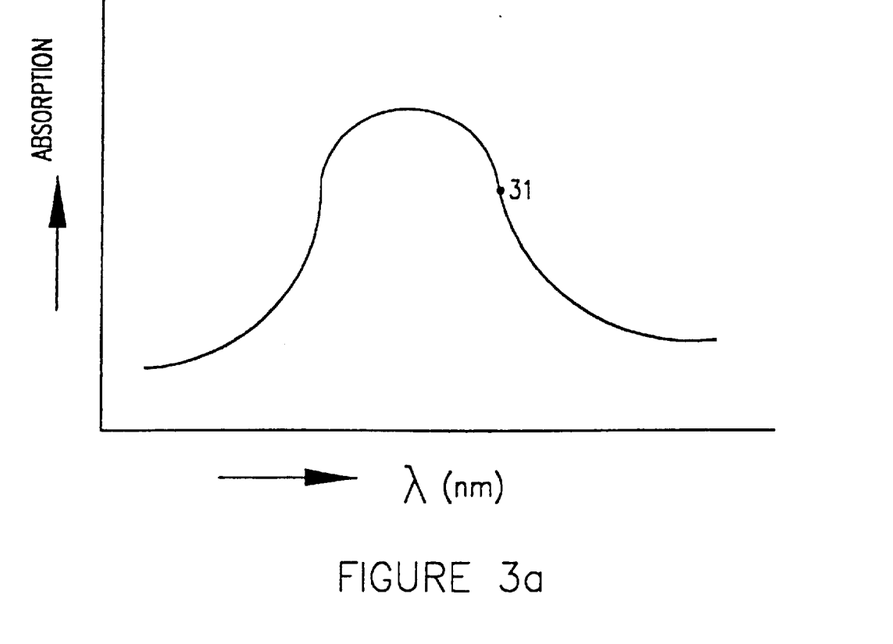
FIG. 3a graphically presents a typical photosensitizer with broad absorption properties.
Figure 3B:
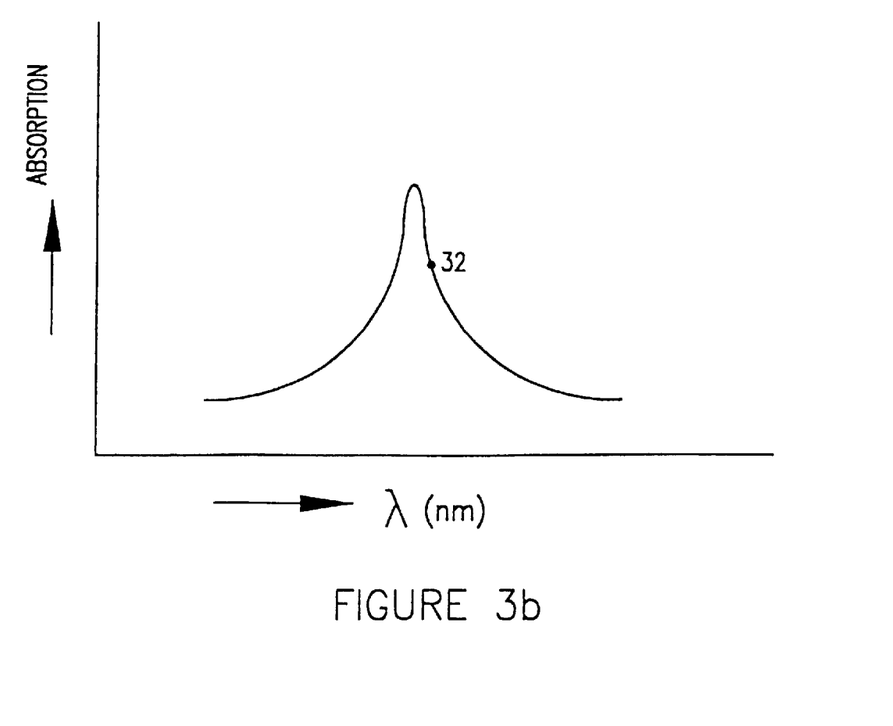
FIG. 3b graphically illustrates a typical photosensitizer with narrow absorption properties.

Although the increase in wavelength is relatively small, it could affect the efficacy of a PDT treatment depending on the absorption properties of a chosen photosensitizer. For example, a photosensitizer with a large absorption over a broad wavelength range, such as one represented in FIG. 3a, may not be affected by a small increase in wavelength due to temperature increases in the system. However, a photosensitizer with an absorption curve like that shown in FIG. 3b, that only absorbs a suitable amount of radiation over a narrow wavelength range is likely to be largely affected by small changes in wavelength due to temperature increases in the system. Also, if the diode laser emission wavelength falls on the decreasing slope of either photosensitizer, such as at point 31 or 32, small increases in the emission wavelength of the diode laser emitter could prohibit effective activation of either photosensitizer, although the effect would be more profound for the photosensitizer shown in FIG. 3b. It is thus advantageous to employ a photosensitizer with broad absorption properties over a broad range of wavelengths. However, if a photosensitizer with narrow absorption properties over a narrow range of wavelengths must be used for a certain application, the present invention provides a device that could increase the relative amount of photosensitizer activated. The present invention minimizes thermal gain and therefore, it is easier to maintain the diode laser emitter at the pre-selected wavelength. Thus, the wavelength remains stable and is not increased to a non-activating wavelength, i.e. outside a chosen photosensitizer's absorption range.

FIG. 2 illustrates that the system operating at a duty factor of 50% yields the greatest average output power of approximately 4.41 watts at 24 amps. It is clear that the system operating non-continuously achieves much greater average output power than when operated continuously. At 24 amps of input current, the system operating at a 60% duty factor yielded 4.33 watts of average output power, 4.08 watts at 40%, 3.98 watts at 70%, and 3.34 watts at 30%. At 24 amps, the system operating at a 50% duty factor yields an average output power 500% greater than when operating continuously with a aluminum nitride thermoplastic pad (average output power, 0.82 amps), and 2700% greater than with a indium foil pad (average output power, 0.16 amps).

The average output powers for the system operating at various duty factors are related to the peak output powers shown in FIG. 1. After the system reaches the threshold current, the average output power for the system operating at a given duty factor and peak current is equivalent to the product of the peak output power of the system at that duty factor and current, and the duty factor. For example, the diode laser emitter group having a duty factor of 50%, a peak injection current of 24 amps, and a peak output power of 8.82 watts, yields an average output power of (0.50)(8.82 watts)=4.41 watts.

Also, illustrated in both FIGS. 1 and 2, when the system is operated continuously, it reaches a point, graphs F and G in FIG. 1 for example, when increased input currents do not necessarily lead to an increase in output power. The system is said to be "saturated", and where greater outputs are necessary, this is disadvantageous. However, if stable output power is required for a certain application, curves exhibited by the system operating continuously may be advantageous because if the input current cannot be adequately controlled, output powers will essentially remain the same if near the saturation point. This is in contrast to the curves exhibited by the system operating non-continuously where small increases or decreases in input current can lead to large changes in output power. Therefore, if stable output power is required, and it is necessary to operate the system at a duty factor, a stable current source must be employed.

Figure 4A:
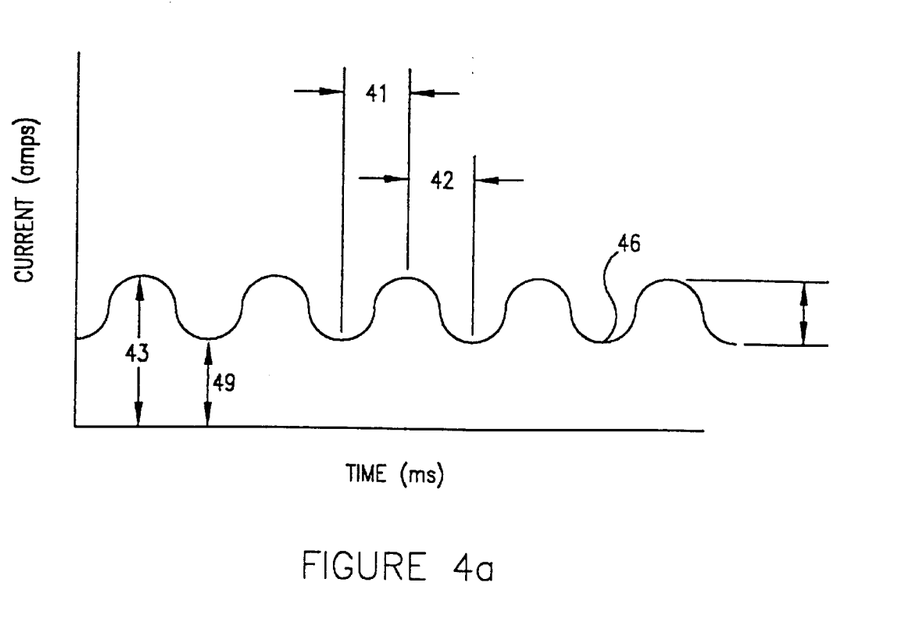
FIG. 4a graphically displays the relationship of current vs. time of a diode laser emitter or emitter group with a 50% duty factor FIG. 4b graphically shows the relationship of current vs. time for a diode laser emitter or emitter group with a 40% duty factor.
Figure 4B:
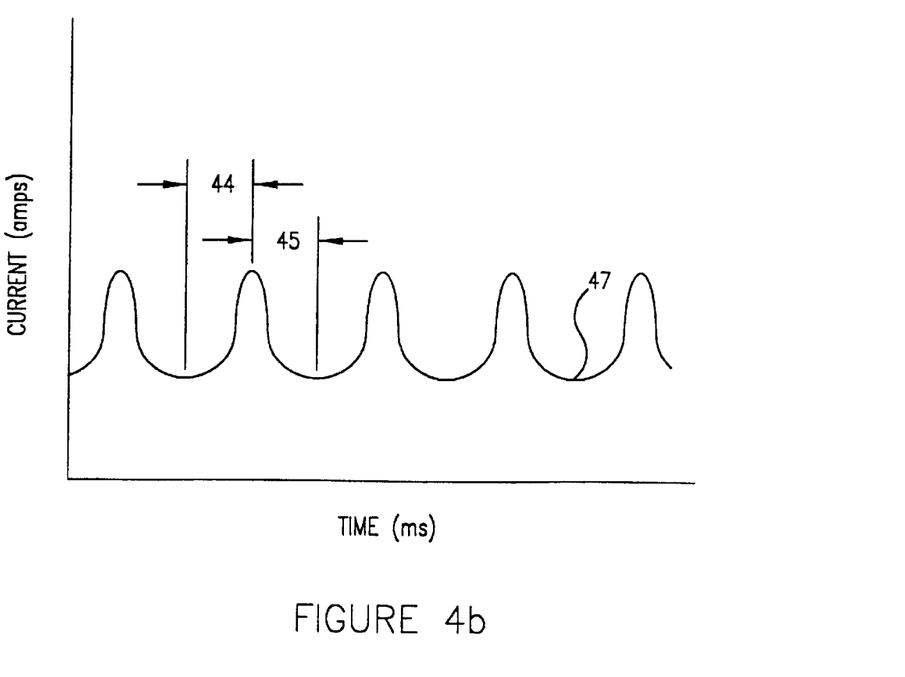

In both FIGS. 1 and FIG. 2, the system is operating at a high repetition rate of 1 kHz. This corresponds to 1 ms cycles, which are characterized by the various duty factors. FIGS. 4a and 4b graphically illustrates this characterization. FIG. 4a shows a graph of injection current vs. time for a diode laser emitter with 50% duty factor. Distances 41 and 42 are equal, indicating that the diode laser emitter is injected with current essentially 50% of the time. Thus, since the system is operating at 1 KHz, and the sum of 41 and 42 is one cycle, distances 41 and 42 represent times of approximately 500 (s.

For comparison, FIG. 4b displays a graph of injection current vs. time for a diode laser emitter operating at a 40% duty factor. Distances 44 and 45 are not equal because current injection takes place over a shorter time than the dormant period. The sum of distances 44 and 45 represent one cycle, and since the system is operating at 1 kHz and distance 44 is 40% of one cycle, it represents a time of about 400 (s, and 45 represents a time of about 600 (s. Although both FIG. 1 and 2 illustrate a system operating at 1 kHz, the system may be operated at slower or faster repetition rates depending on the necessary output characteristics for a chosen application. For example, if only near cw output is necessary, the system can be operated <1 kHz, but if more cw output is needed, the system should be operated >1 kHz.

Alternatively, the continuity of the output may be modified through manipulation of the number of diode laser emitters or emitter groups. Efficiency may be increased by limiting the duty factor of the diode laser emitter or emitter groups but including a large enough number of emitters or emitter groups to still maintain the desired output. The method chosen for achievement of output power is dictated by a chosen application and the desired efficiency of operation. For example, some applications do not even require a near-continuous wave output, and less diode laser emitter or emitter groups, and/or a lower duty factor can be used.

Employing diode laser emitters or emitter groups less than 100% of the time may create an undesired on-off pattern if an application requires a cw source. Continuous wave sources are preferred in PDT because they can be evenly applied at the treatment site to yield reproducible results and limited treatment times. Moreover, a cw source maintains the greatest amount of photosensitizer in an excited state, and therefore more oxygen singlets are formed which can cause tissue necrosis. To compensate for the disadvantageous on-off pattern, transistors can be used to intermittently activate different diode laser emitters or emitter groups. In this manner, a quasi-continuous wave output from a treatment fiber can be achieved if all diode laser emitter outputs are multiplexed into a single fiber.

If high repetition rates are employed, it may not be necessary to use transistors to intermittently drive successive diode laser emitters or emitter groups. Rather, a nearly continuous source is achievable simply by multiplexing the output or outputs of the simultaneously driven diode laser emitters or emitter groups. As the repetition rate is decreased, the off time of a diode laser emitter or emitter group increases for a given duty factor, which may be disadvantageous if a cw source is needed for an application. However, with fast repetition rates, even systems operating at small duty factors (<50%) have short off times, and can have the same effects of a quasi-cw or cw system. For example, a system operating at a 50% duty factor is off for 500 (s at 1 kHz, and off for only 0.5 (s at 1 GHz. If a system employs transistors to switch the current between diode laser emitter or emitter groups, advantageous effects may still be realized if there any gaps between the outputs of the diode laser emitters or emitter groups.

The number of diode laser emitters or emitter groups necessary to create quasi-continuous output is directly related to the duty factor used for the diodes. For example, at least four diode laser emitters or emitter groups with a duty factor of 30% must be combined, but only two diode laser emitters or emitter groups with a duty factor of 50% must be combined to gain the advantages of quasi-cw output. Additionally, different combinations of duty factors may be used in combination with high tech software programs. For example, two diode laser emitters or emitter groups with a 30% duty factor in combination with one diode laser emitter or emitter group with a 40% duty factor can simulate quasi-continuous wave output. Adding diode laser emitters or emitter groups increases the average power output of the system, which may be disadvantageous in certain applications such as PDT where high powers may ablate the tissue in addition to or instead of activating the chosen photosensitizer.

Since operation of laser diodes at currents below the peak value, 24 amps, can enhance (extend) the lifetime and reliability of the diode lasers, and yield more reproducible results—choosing two diode laser emitter groups operating at a 50% duty factor leads to a more efficient average output than employing a single emitter group which produces equivalent average output power. In the current example illustrated in FIG. 1 and 2, a system having two diode laser emitter groups operating at intermittent 50% duty factors yields 3.76 watts of average output power at 17.5 amps of injection current. A single diode laser emitter group operating at a 50% duty factor requires 22 amps of input current to produce equivalent power. Increased injection currents can lead to the undesired effects described above, and therefore, it is advantageous to employ the system having two diode laser emitter groups.

Figure 5:
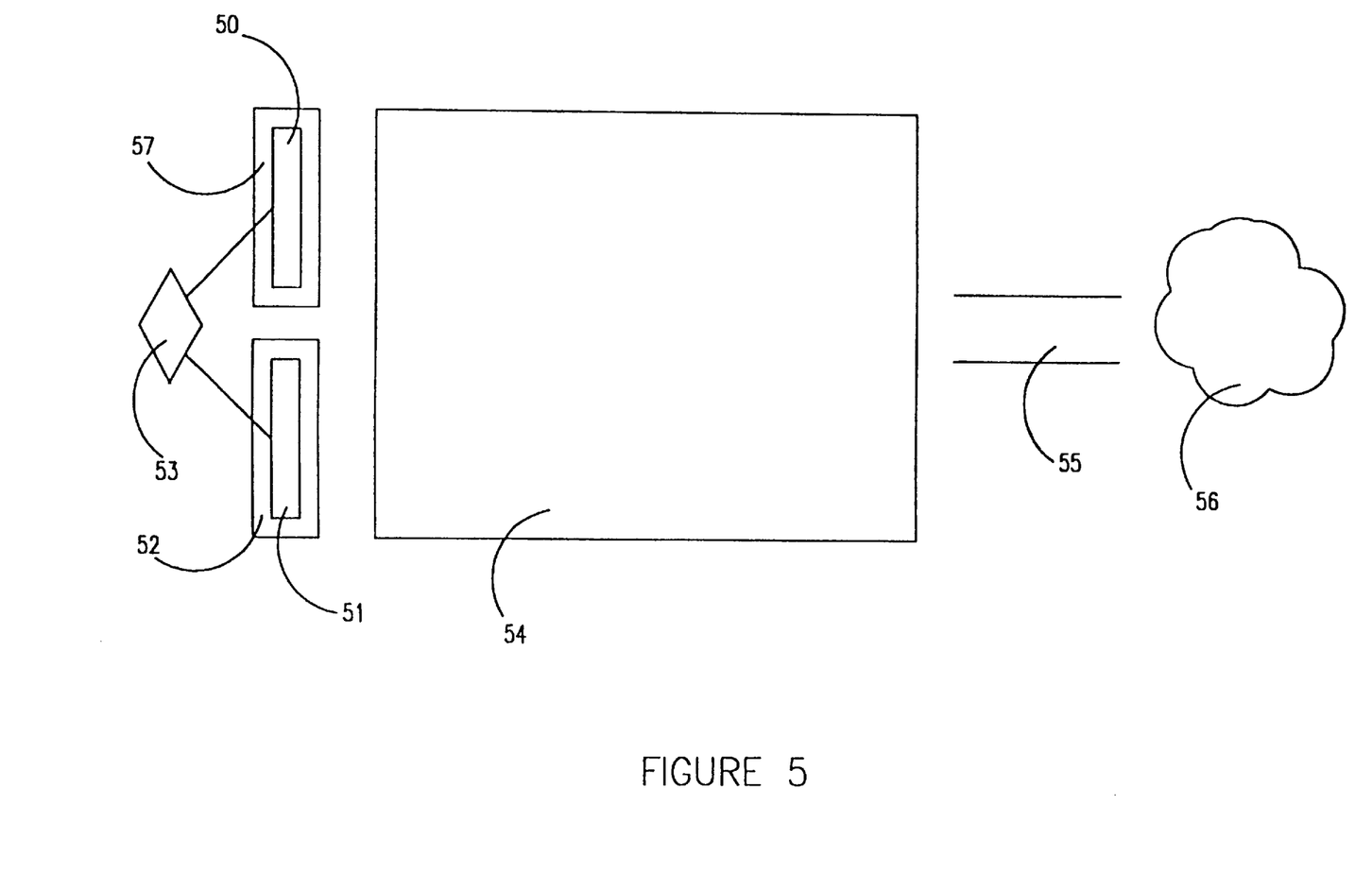
FIG. 5 displays an embodiment of the present invention.

An embodiment of the present invention employing diode laser emitter groups operating at a 50% duty factor is displayed in FIG. 5. Radiation from two diode laser emitter groups 50, 51 is used to activate a photosensitizer at treatment site 56. Since 50% duty factor diode laser emitter groups 50, 51 are used in this embodiment, only two are necessary to achieve quasi-cw output. Fast switching transistor 53 alternates injection currents between diode laser emitter groups 50, 51 at nearly equivalent rates to create quasi-cw output, although standard transistors may be employed. For a system operating at 1 kHz, diode laser emitter groups 50, 51 are injected with current for about 500 μs. Thus, while one diode laser emitter group is being injected with current, the other rests for about 500 μs. Diode laser emitter groups 50, 51 are mounted respectively on substrates 57, 52. Substrates 52, 57 may be a heat sink surrounded by a water cooling system which pumps low temperature water, 15° C. for example, through the laser system to conduct away thermal energy generated by diode laser emitter groups 50, 51.

In addition to fast switching transistor 53, multiplexing is useful to achieve quasi-cw output necessary for applications in PDT, particularly activation of photosensitizers that have absorption peaks in the 600–760 nm range. Any suitable optical coupling system may be employed to multiplex the radiation into a single fiber. For example, Neuberger et. al teaches an integrated combiner system in U.S. Pat. No. 5,668,903, represented by 54 in FIG. 5. Radiation emitted from diode laser emitter groups 50, 51, is transmitted through integrated combiner system 54 and coupled into fiber 55 which transmits the radiation to treatment site 56.

Figure 6:
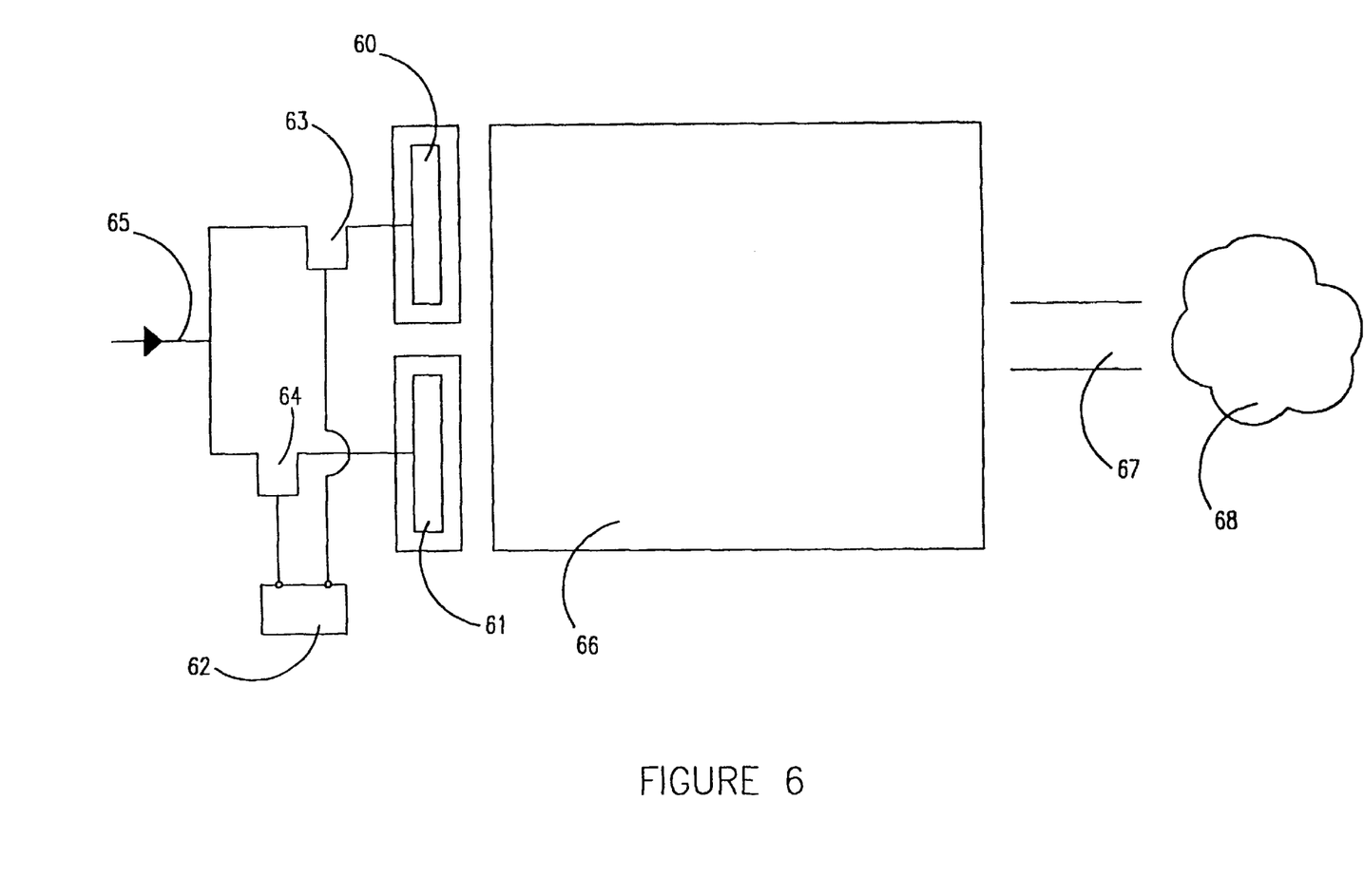
FIG. 6 illustrates a preferred embodiment of the present invention.

FIG. 6 illustrates another preferred embodiment of the present invention. It is similar to FIG. 5, but the embodiment shown here employs two transistors 63, 64. Rather than flipping the current between two diode laser emitters or emitter groups, injection current 65 to diode laser emitter groups 60, 61 can be intermittently controlled by transistor control unit 62. Thus, instead of switching the currents, transistors 63, 64 act as valves to allow injection current 65 to diode laser emitter groups 60, 61. Diode laser emitter groups 60, 61 emit radiation which integrated combiner system 66, described in '903, couples into single fiber 67. Radiation from single fiber 67 is utilized to activate a chosen photosensitizer at treatment site 68. This embodiment is advantageous compared to FIG. 5 because the employment of transistor control unit 62 with transistors 63, 64 eliminates any time fast switching transistor 53 of FIG. 5 may need to switch the current. Also, fast switching transistor 53 may be limited if high drive currents are necessary, i.e. above 20 amps.

In another embodiment of the beam combiner concept within the scope of the present invention, optical microelectromechanical system (optical MEMS) technology is used to create fast switching elements which can select and direct outputs from multiple lasers into a treatment optical fiber. Such optical elements are switched simultaneously with the powering of the diode emitters to select and direct output from the activated diode emitter to the treatment fiber. The switching function might simply cause the element to flip in or out of the light path from the selected diode emitter. Alternatively, a switching element may function by changing from a transparent to a reflective component in the directed path of the selected diode emitter.

The present invention may also be used in combination with the modular laser system disclosed in U.S. Pat. No. 5,771,325 by Wolfgang Neuberger. Neuberger teaches a system wherein diode laser emitters or emitter groups can be interchanged without shutting down the system. Multiple diode laser emitters or emitter groups can be employed in the present invention so that their duty factors add to greater than 100%. A quasi-cw system is thus available at all times, even during diode laser emitter or emitter group failure, because as the diode laser emitter or emitter groups is being replaced, the operating diode laser emitters or emitter groups have successive duty factors that add to at least 100%. Additionally, the duty factor of the operating diode laser emitters or emitter groups can be raised during replacement so quasi-cw output is available. For example, for a system with five diode emitter groups operating at a 20% duty factor, while one of the emitter groups is being replaced, the duty factor of the other four emitter groups can be increased to 25%.

Since radiation from the diode laser emitters or emitter groups is multiplexed into a single fiber, the present invention allows for a very narrow and flexible high power transmission system. This is very advantageous in many medical applications including PDT where the laser system delivery component must be guided through narrow passages to far reaching points in a mammalian body. Fewer fibers are necessary, and the diameter of the delivery component is decreased, which substantially increases the flexibility and maneuverability of the delivery component.

It is clear to one skilled in the art that as material science improves, larger duty factors may become increasingly efficient, and fewer diode laser emitters or emitter groups may be necessary to create equivalent power. It should also be evident that the present system may be employed for PDT in animals as well as humans.

Having described preferred embodiments of the invention with reference to the accompanying drawings, it is to be understood that the invention is not limited to these precise embodiments, and that various changes and modifications may be effected therein by one skilled in the art without departing from the scope or spirit of the invention as defined in the appended claims.

What is claimed is:

1. A diode laser system comprising:
   at least two diode laser emitters, which produce respective outputs when injected with a drive current;
   at least one substrate;
   means to intermittently inject emitters with drive current at a predetermined repetition rate;
   means to optically combine said respective outputs;
   wherein said at least two diode laser emitters are mounted on said at least one substrate;
   wherein said at least two diode laser emitters are intermittently injected with drive current by said means to intermittently inject said emitters with drive current to produce respective outputs;
   wherein said at least two diode laser emitters operate at individual duty factors of less than 100%; and,
   wherein said respective outputs from said at least two diode laser emitters are optically combined by said means to optically combine said respective outputs.

2. A diode laser system according to claim 1, further comprising at least one transistor, wherein said at least two diode laser emitters are intermittently injected with drive current by said at least one transistor.

3. A diode laser system according to claim 2 wherein said at least two diode laser emitters individually operate at duty factors that add to at least 100%.

4. A diode laser system according to claim 2 wherein said at least one transistor is a fast switching transistor.

5. A diode laser system according to claim 4 wherein said at least two diode laser emitters individually operate at said duty factors that add to at least approximately 100%.

6. A diode laser system according to claim 1 wherein said respective outputs have a common wavelength ranging from visible red to near IR.

7. A diode laser system according to claim 1 wherein said at least two diode laser emitters are operated at a duty factor of 30–70%, and preferably at 50–60%.

8. A diode laser system according to claim 1 further comprising a modular laser subsystem wherein:
   said at least two diode laser emitters operate in parallel;
   said means to intermittently inject said emitters with drive current provides said drive current in parallel to said at least two diode laser emitters; whereby
   said drive current may be discontinued to at least one non-functioning diode laser emitter while continuing said drive current to at least one functioning diode laser emitter; and whereby
   said at least one non-functioning diode laser emitters may be replaced without shutting off said diode laser system.

9. A diode laser system according to claim 8 wherein said duty factor of each said functioning diode laser emitter is increased by increasing said repetition rate of said drive current injected into said functioning diode laser emitters while replacing said at least one non-functioning diode laser emitters to compensate for said at least one non-functioning diode laser emitters.

10. A diode laser system according to claim 1 wherein said respective outputs have a common wavelength ranging form 3.0 to 3.5 $\mu$m.

11. A diode laser system comprising;
   at least two diode emitter groups;
   each said diode emitter group comprising at least two diode laser emitters, which produce outputs when injected with a drive current,
   said outputs combine to produce a respective output of each said diode emitter group,
   at least one substrate;
   at least one means to intermittently inject said emitters with drive current at a repetition rate of at least approximately 1 kHz,
   means to optically combine said respective outputs;
   wherein, said at least two diode laser emitters are mounted on said at least one substrate;
   wherein said at least two diode laser emitters are connected in series;
   wherein said at least two diode laser emitters groups are simultaneously and intermittently injected with drive current by said means to intermittently inject said emitters with drive current to produce said respective outputs;

wherein said at least two diode laser emitter groups operate at individual duty factors of less than 100%;

whereby said duty factors limit generation of thermal energy by said diode laser emitter groups; and said respective outputs from said at least two diode laser emitter groups are optically combined by said means to optically combine said respective outputs and connected to a single optical delivery fiber.

12. A diode laser system according to claim 11, further comprising at least one transistor, wherein said transistor intermittently switches said drive current between said at least two diode laser emitter groups.

13. A diode laser system according to claim 12 wherein said at least two diode laser emitter groups individually operate at duty factors that add to at least approximately 100%.

14. A diode laser system according to claim 12 wherein said at least one transistor is a fast switching transistor.

15. A diode laser system according to claim 11 wherein said at least two diode laser emitter groups are operated at a duty factor of 30–70%, and preferably at 50–60%.

16. A diode laser system according to claim 11 further comprising a modular laser sub-system wherein: said at least two diode laser groups operate in parallel; said means to intermittently inject said emitter with drive current provides said drive current in parallel to said at least two diode laser emitter groups;

whereby said drive current may be discontinued to ay least one non-functioning diode laser emitter group while continuing said drive current to at least one functioning diode laser emitter group; and whereby said at least one non-functioning diode laser emitter group may be replaced without shutting off said diode laser system.

17. A diode laser system according to claim 16 wherein said at least two diode laser emitter groups individually operate at duty factors that add to at least approximately 100%.

18. A diode laser system according to claim 17 wherein said duty factor of each said functioning diode laser emitter group is increased by increasing said repetition rate of said drive current injected into said diode laser emitter groups while replacing said at least one non-functioning diode laser emitter group to compensate for said at least one non-functioning diode laser emitter groups.

19. A diode laser system according to claim 11 wherein said outputs have a wavelength no greater than about 760 nm.

* * * * *